US008304205B2

(12) United States Patent
Kappel et al.

(10) Patent No.: US 8,304,205 B2
(45) Date of Patent: Nov. 6, 2012

(54) BLOOD COAGULATION ASSAYS

(75) Inventors: Andreas Kappel, Königstein (DE);
Andrea Lichte, Marburg (DE); Norbert Zander, Marburg (DE); Stefan Teigelkamp, Niederwalgern (DE);
Sabine Teigelkamp, legal representative, Niederwalgern (DE); Carsten Schelp, Hockessin (DE)

(73) Assignee: Siemens Healthcare Diagnostics Products GmbH (DE)

( * ) Notice: Subject to any disclaimer, the term of this patent is extended or adjusted under 35 U.S.C. 154(b) by 251 days.

(21) Appl. No.: 12/569,714

(22) Filed: Sep. 29, 2009

(65) Prior Publication Data

US 2010/0086953 A1    Apr. 8, 2010

(30) Foreign Application Priority Data

Oct. 2, 2008  (EP) .................................. 08017334

(51) Int. Cl.
*C12Q 1/56*        (2006.01)
*G01N 33/53*       (2006.01)

(52) U.S. Cl. ......... 435/13; 435/7.72; 435/212; 435/214; 435/215; 435/216; 435/217; 435/219

(58) Field of Classification Search ................. 435/7.72, 435/13, 212, 214, 215, 216, 217, 219
See application file for complete search history.

(56) References Cited

U.S. PATENT DOCUMENTS

| | | | |
|---|---|---|---|
| 5,340,716 A | | 8/1994 | Ullman et al. |
| 5,580,744 A | | 12/1996 | Zweig |
| 5,627,038 A | * | 5/1997 | Hemker ...................... 435/7.21 |
| 5,929,049 A | | 7/1999 | Singh et al. |
| 6,153,442 A | | 11/2000 | Pirio et al. |
| 7,172,906 B2 | | 2/2007 | Teng et al. |
| 2003/0027235 A1 | | 2/2003 | Kraus et al. |
| 2004/0203163 A1 | * | 10/2004 | Cohen et al. .................... 436/69 |
| 2005/0118727 A1 | | 6/2005 | Schelp et al. |
| 2006/0182735 A1 | * | 8/2006 | Metzner et al. ............ 424/94.64 |
| 2007/0207960 A1 | * | 9/2007 | Blajchman et al. ............. 514/12 |
| 2010/0166729 A9 | * | 7/2010 | Madison et al. ........... 424/94.64 |

FOREIGN PATENT DOCUMENTS

| | | |
|---|---|---|
| DE | 102004042124 A1 | 3/2006 |
| EP | 0515194 A2 | 11/1992 |
| EP | 0924523 A2 | 6/1999 |

OTHER PUBLICATIONS

Morrissey Lab Protocols—Factor Vila Enzymatic Activity-I (version: Aug. 17, 2004; http://tf7.org/mlabprotocols.htm).*
Morrissey Lab Protocols—Factor Vila Enzymatic Activity-I I (version: Aug. 17, 2004; http://tf7.org/mlabprotocols.htm).*
Davie E.W., et.al., The coagulation cascade: Initiation, Maintenance, and Regulaion, Biochemistry (1991) 30, No. 43, 10363-10370.*
Morrissey J.H.,et.al., Quantitation of Activated factor VII Levels in Plasma Using a Tissue Factor Mutant Selectively Deficient in Promoting factor VII Activation, Blood (1993) 81, No. 3, 734-744.*
Kario K.,et.al., Fluorogenic Assay of Activated Factor VII: Plasma Factor VIIa Levels in Relation to Arterial Cardiovascular Diseases in Japanese, Arterioscler. Thromb. (1994) 14, 265-274.*
Peppard J.,et.al., Development of a High-Throughput Screeninng Assay for Inhibitors of Aggrecan Cleavage Using Lumisescent Oxygen Channeling (AlphaScreen™. J Biomolecular Screening, (2003) 8, 149-156.*
Eglen R M, et.al., The Use of AlphaScreen Technology in HTS: Current Status. Current Chemical Genomics, (2008) 1, 2-10.*
spectrozyme FXa from American Diagnostica inc downloaded from http://search.cosmobio.co.jp/cosmo_search_p/search_gate2/docs/ADI_/222.20110621.pdf Jan. 16, 2012 (1 page).*
van Wijk et al. Clin. Chem. (1980) 26(7): 885-890.*
defintion of a kit downloaded from Dictionary.com at http://dictionary.reference.com/browse/kit on Jan. 16, 2012 (2 pages).*
Machine translation of DE 10200402124 downloaded from the EPO Jun. 28, 2012.*
Principles of Alpha Screen ™, Perkin Elmer, 2003.
Cuatrecasas, R, Protein Purification by Affinity Chromatography, The Journal of Biological Chemistry, vol. 245, No. 12, Issue Jun. 25, pp. 3059-3065, 1970.

* cited by examiner

*Primary Examiner* — Susan Hanley
(74) *Attorney, Agent, or Firm* — Noam R. Pollack (57) ABSTRACT

The invention relates to methods for determining the activity of a proteolytic coagulation factor of the blood coagulation cascade in a body fluid such as whole blood or plasma. A combination is provided in a reaction mixture. The combination comprises the sample and an activation agent for activating a proteolytic coagulation factor of the blood coagulation cascade or for activating the blood coagulation cascade. The effect of the activating on a reagent system comprising a cleavable moiety is evaluated. The cleavable moiety is or becomes bound to a chemiluminescent agent or a sensitizer agent or both. The chemiluminescent agent and the sensitizer agent are related in that, when in close proximity, energization of the sensitizer agent results in energization of the chemiluminescent agent. The effect of the activating is related to the activity of a proteolytic coagulation factor of the blood coagulation cascade wherein the effect is the extent of cleavage of the cleavable moiety.

12 Claims, 6 Drawing Sheets

BLOOD COAGULATION ASSAYS

This application claims priority to European Application No. 08017334, filed Oct. 2, 2008, which is incorporated herein by reference.

The invention relates to methods for determining the activity of a proteolytic coagulation factor of the blood coagulation cascade in a body fluid such as whole blood or plasma.

The process of blood clotting and the subsequent dissolution of the clot, following repair of the injured tissue, is termed hemostasis, which is a highly complex process that involves both cellular and biochemical components. Hemostasis is composed of four major events that occur in a set order following vascular injury. Coagulation is initiated almost instantly after an injury to the blood vessel damages the endothelium. The initial phase of the process is referred to a vascular constriction, which limits the flow of blood to the area of injury. Next, platelets become activated by thrombin and immediately aggregate at the site of injury to form a hemostatic plug at the site of injury; this process is called primary hemostasis. The formation of the plug is stimulated by the protein fibrinogen. Secondary hemostasis occurs simultaneously; proteins in the blood plasma, called coagulation factors, respond in a complex cascade to form fibrin strands, which strengthen the platelet plug. The coagulation factors act in two intimately linked cascades, referred to as the extrinsic and intrinsic pathways. Initial diagnostic testing of patients with suspected bleeding disorders is usually performed with the so called global coagulation tests, the partial activated thromboplastin time (aPTT) and the prothrombin time (PT). In addition, these tests are also used for anticoagulant therapy monitoring. While the aPTT is mainly used for detection of deficiencies in factors of the intrinsic pathway and for heparin therapy monitoring, the PT is used for detection of deficiencies in factors of the extrinsic pathway and for vitamin K antagonist therapy monitoring. Both, aPTT and PT, can also be used for detection of single factor deficiencies by mixing a plasma that is deficient for the coagulation factor to be quantified with the patient sample.

Many patients with inherited bleeding disorders have prolongation of the aPTT, the PT, or both. A patient with a prolonged aPTT and a normal PT is considered to have a defect in the intrinsic coagulation pathway. The name indicates that all of the components of the aPTT test, except kaolin, are "intrinsic" to the plasma. On the other hand, a patient with a prolonged PT and a normal aPTT has a defect in the extrinsic coagulation pathway (tissue factor is "extrinsic" to the plasma). Prolongation of both the aPTT and the PT suggests that the defect lies in a common pathway.

In the PT reaction, coagulation is initiated in a patient plasma sample by activation of the extrinsic pathway, i.e. by addition of a mixture of tissue factor, phospholipids and calcium ions. Subsequently, the time until the thrombin that is generated has converted enough fibrinogen to a visible fibrin clot is determined. This is a relatively insensitive detection method that also requires high sample volumes.

The extrinsic (or tissue factor) pathway generates a "thrombin burst", which is a process by which thrombin, the most important constituent of the coagulation cascade in terms of its feedback activation roles, is released instantaneously. Following damage to the blood vessel or tissue, Tissue Factor (TF) is released, forming a complex with Factor VII and activating it. The TF-Factor VIIa complex then activates Factors IX and X. Factor Xa and its co-factor Factor Va form the prothrombinase complex, which activates prothrombin to thrombin. Thrombin subsequently activates other components of the coagulation cascade, including Factors V and VII, and activates and releases Factor VIII from being bound to von Willebrand Factor (vWF). Ultimately, thrombin converts fibrinogen to insoluble fibrin and thereby generates a clot. Factor XIII subsequently stabilizes the fibrin clot.

The intrinsic (or contact activation) pathway begins with formation of the primary complex consisting of high-molecular weight kininogen (HMWK), prekallikrein, and Factor XII. Prekallikrein is converted to kallikrein and activates Factor XII to Factor XIIa. Factor XIIa converts Factor XI into Factor XIa, Factor XIa activates Factor IX, which together with its co-factor Factor VIIIa form the tenase complex, which activates Factor X to Factor Xa. As in the extrinsic pathway, Factor Xa and its co-factor Factor Va form the prothrombinase complex, which again activates prothrombin to thrombin.

The concept of "intrinsic" and "extrinsic" pathways has served for many years as a useful model for coagulation. Evidence has shown that the pathways are not redundant but are highly interconnected. For example, the tissue factor/Factor VIIa complex activates not only Factor X but also Factor IX of the intrinsic pathway. Furthermore, patients with severe Factor VII deficiency may bleed even though the intrinsic pathway is intact. In addition, the severe bleeding associated with deficiencies of Factor VIII or IX would not necessarily be expected if the extrinsic pathway alone were sufficient to achieve normal hemostasis. The intrinsic and extrinsic systems converge at Factor X to a single common pathway that is ultimately responsible for the production of thrombin (Factor IIa). Although they are initiated by distinct mechanisms, the intrinsic and extrinsic pathways converge on a common pathway that leads to clot formation.

The exact quantification of the biochemical activities of both the entire extrinsic and intrinsic pathways as well as of their respective coagulation factors is highly important for the diagnosis of bleeding disorders, thrombophilia, and also for anticoagulant therapy monitoring, and the like. Current test methods for the pathways activity usually measure photometrically the time until a fibrin clot appears, after the respective pathway has been triggered in a plasma sample. Modified versions of this basic principle exist for the quantification of the activities of single coagulation factors. These photometric methods often lack the sensitivity that is required for the exact quantification of low quantities of certain coagulation factors such as Factor VIII, generally require high sample volumes, and can therefore only be performed with plasma and not whole blood samples.

Another group of test methods are chromogenic tests that measure the enzymatic or cofactor activity of coagulation factors. In these tests, chromogenic peptides are used that can be specifically cleaved by coagulation factors, thereby releasing a quencher molecule that inhibits the action of the chromophore, which results in a color change that can be quantified photometrically. These methods share similar restrictions that exist for clot-detection assays, i.e. low sensitivity and incompatibility with whole blood samples. Modifications of this protocol that employ other detection technologies (e.g., fluorescence resonance energy transfer or FRET) have been described. It is not clear whether these methods overcome the restrictions of the tests based on chromophore/quencher peptide conjugates or whether these methods are effective with real patient samples, as these methods have only been evaluated with purified components. Furthermore, methods involving FRET possess the technical difficulties such as difficulty in synthesis of substrates for FRET, difficulty in spacing of the donor and acceptor moieties in FRET using peptide sequences, need for larger sample volumes, the problems associated with interference, the use of plasma and not whole blood samples, and so forth. Another general problem of the chromogenic and FRET assays described above is that the peptides used have to be relatively short. This limits the specificity for their cognate proteolytic coagulation factor and makes these assays vulnerable to wrong test results, as these peptides are not only cleaved by one specific proteolytic coagulation factor but rather are susceptible to cleavage by multiple proteolytic enzymes.

Another test method for detecting hemostasis disturbances is described in US 2003/0027235 A1 (Kraus et al.) wherein as a consequence of the platelet aggregation or clot formation reaction in an activated plasma sample, substances of a signal-generating system are brought to a distance from each other which permits an interaction between the substances which leads to generation of a measurable signal.

There is, therefore, a continuing need to develop fast and accurate diagnostic methods to ascertain the activity of a proteolytic coagulation factor of a coagulation cascade in patient samples, particularly reflecting in vivo activity, which can be related to the presence and/or amount and/or activity of such proteolytic coagulation factor. The methods should be fully automated and be accurate even when conducted on whole blood samples.

SUMMARY

The present invention relates to a method for determining the activity of a proteolytic coagulation factor of the blood coagulation cascade in a sample. A combination is provided in a reaction mixture. The combination comprises (i) the sample, (ii) an activation agent for activating directly or indirectly a proteolytic coagulation factor of the blood coagulation cascade, (iii) a cleavable moiety which has a cleavage site that is cleavable by the activated proteolytic coagulation factor, (iv) a chemiluminescent agent, and (v) a sensitizer agent. The cleavable moiety is or becomes bound to the chemiluminescent agent or the sensitizer agent or both. The chemiluminescent agent and the sensitizer agent are related in that, when in close proximity, energization of the sensitizer agent results in energization of the chemiluminescent agent. The sensitizer reagent is energized and the chemiluminescent signal being generated in the reaction mixture is measured and related to the activity of the proteolytic coagulation factor. The chemiluminescent signal is inversely proportional to the activity of the activated proteolytic coagulation factor.

In some embodiments the cleavable moiety is a naturally occurring substrate of the activated proteolytic coagulation factor and is endogenously present in the sample, i.e. the cleavable moiety is added to the reaction mixture by addition of the sample to the reaction mixture. In these embodiments the cleavable moiety becomes bound to the chemiluminescent agent and the sensitizer agent in the reaction mixture.

In some embodiments the cleavable moiety is contained in a separate reagent which is added to the reaction mixture. In these embodiments the cleavable moiety is preferably a synthetic entity, most preferably a peptide.

In some embodiments the activity of the activated proteolytic coagulation factor is indicative of the presence or activity of one or more components of the sample to be analyzed that influence the activity of the proteolytic coagulation factor. In some embodiments the sample is mixed with plasma or whole blood that is deficient in a single component that influences the activity of the proteolytic coagulation factor and the activity of the proteolytic coagulation factor is indicative of the presence or activity of the single component in the sample. In some embodiments the activity of the activated proteolytic coagulation factor is indicative of the functionality of the intrinsic or the extrinsic blood coagulation pathway. In some embodiments the activity of the activated proteolytic coagulation factor is indicative of the presence of one or more therapeutic anticoagulants.

Another embodiment of the present invention is a method for assessing an activation property or inhibitory property of a substance on one or more proteolytic coagulation factors of the blood coagulation cascade. A combination is provided in a reaction mixture. The combination comprises the sample containing one or more proteolytic coagulation factors of the blood coagulation cascade, a cleavable moiety which has a cleavage site that is cleavable by an activated proteolytic coagulation factor, a chemiluminescent agent, a sensitizer agent and the substance to be tested. The cleavable moiety is or becomes bound to a chemiluminescent agent or a sensitizer agent or both. The chemiluminescent agent and the sensitizer agent are related in that, when in close proximity, energization of the sensitizer agent results in energization of the chemiluminescent agent. The sensitizer agent is energized and the chemiluminescent signal being generated in the reaction mixture is measured and related to the activation or inhibitory property of the substance on the one or more proteolytic coagulation factors of the blood coagulation cascade. To evaluate the activation or inhibitory property of the substance to be tested the chemiluminescent signal being generated in a reaction mixture to which the substance to be tested is not added is measured.

The present methods overcome many problems associated with known coagulation assays. Coagulation assays conducted in accordance with the present disclosure are highly sensitive. The present assays require only small sample volumes and, therefore, may be performed with whole blood samples as opposed to plasma samples that are currently used. Moreover, other problems associated with high sample volumes, like high hemoglobin concentrations or icteric or lipaemic samples (referred to as HIL interference) are also circumvented while maintaining a high sensitivity. Furthermore, the present methods solve the problems associated with the poor sensitivity of many of the currently used methods.

As mentioned above, the present methods provide for determining the activity of a proteolytic coagulation factor of the blood coagulation cascade in a sample. The blood coagulation cascade includes the above-described and well-known intrinsic and extrinsic pathways as well as the common pathway. The methods may be employed to determine the activity (and hence the presence and/or amount) of a specific proteolytic coagulation factor in a sample from a subject, for example, a patient sample. Further, the present methods provide for a general screening technique for analyzing a sample for defects in the extrinsic or intrinsic pathway of the blood coagulation cascade. Having identified a sample with a defect in the intrinsic or extrinsic pathway, e.g. by activating prothrombin to thrombin indirectly by using a PT- or an aPTT-activation agent, and determining a reduced or elevated thrombin activity compared to a normal control, the sample may be analyzed in subsequent experiments to determine the specific component(s) that is/are defective. This can be performed by mixing the sample with plasma or whole blood deficient in the specific component to be tested for and performing the methods outlined above.

The sample to be analyzed may be any sample that is suspected of containing at least one or more proteolytic coagulation factors of the blood coagulation cascade. The sample is typically from a mammalian subject and may be whole blood or plasma. The amount of the sample to be analyzed is about 0.01 µl to about 50 µl, or about 0.1 µl to about 40 µl, or about 0.5 µl to about 30 µl, and so forth. One mammalian subject of particular interest is a human subject although other animal species may also be of interest.

The present assays are normally carried out in an aqueous buffered medium at a moderate pH, generally that which provides optimum assay sensitivity. The pH for the assay medium will usually be in the range of about 4 to about 11, more usually in the range of about 5 to about 10, and preferably in the range of about 6.0 to about 9.0. The pH is dependent on the nature of the component(s) of the blood coagulation cascade, the activation agent, the binding of the binding members of any specific binding pairs, the pH optimum for other reagents of the assay, and so forth. Various buffers may be used to achieve the desired pH and maintain the pH during the determination. Illustrative buffers include borate, phosphate, carbonate, tris, barbital, HEPES, and the like. The particular buffer employed is not critical, but in an individual assay one or another buffer may be preferred. Various ancillary materials may be employed in the above methods. For example, in addition to buffers the medium may comprise stabilizers for the medium and for the reagents employed, binding enhancers, chelating agents, preservatives, salts, specific ions, detergents, blocking reagents, proteins, reducing agents or the like.

The blood coagulation cascade includes the aforementioned intrinsic and extrinsic pathways as well as the common pathway. Thus, the term "blood coagulation cascade" includes the entire cascade or portions thereof. Components of the blood coagulation cascade include entities that are involved in the intrinsic, extrinsic and common pathways as well as those involved in the process of hemostasis in general. The components of the blood coagulation cascade include, for example, procoagulant factors, e.g., von Willebrand Factor (vWF), Factors I (fibrinogen), II (prothrombin), IIa (thrombin), V, Va, VII, VIIa, VIII, VIIIa, IX, IXa, X, Xa, XI, XIa, XII (Hageman factor), XIIa, tissue factor and the like, kallikrein, prekallikrein, HMWK, and so forth. The components of the blood coagulation cascade also include anticoagulant factors and coagulation inhibitors such as, for example, protein C, protein S, antithrombin III, C1-Esterase inhibitor, TFPI, heparin cofactor 2, and the like; fibrinolytic factors and their inhibitors such as, for example, plasminogen, t-PA, prourokinase, PAI-1, u-PA and like, and so forth. The components of the blood coagulation cascade that are primarily of interest are proteolytic coagulation factors. Most of the coagulation factors are serin proteases, while others such as factor V/Va, factor VIII/VIIIa and protein S are cofactors of proteases. Other components of the blood coagulation cascade of interest include stabilizing proteins, transmembrane proteins and cofactors, transglutaminases and so forth.

In the present methods, an activation agent is combined with the sample suspected of containing one or more proteolytic coagulation factors of the blood coagulation cascade. The activation agent is an agent for activating a component of the blood coagulation cascade or for activating the blood coagulation cascade. Direct activation of a proteolytic coagulation factor as discussed herein means that the activation agent activates a specific proteolytic coagulation factor directly without depending on the interaction with other factors that might activate or modulate the specific proteolytic coagulation factor. Indirect activation of a proteolytic coagulation factor as discussed herein means that the activation agent activates the blood coagulation cascade upstream of the proteolytic coagulation factor. The nature of the activating agent is dependent on whether the activation agent directly or indirectly activates a proteolytic coagulation factor of the blood coagulation cascade, the nature of the test to be performed, the component to be analyzed, the cleavage moiety that is used in the test, and so forth. The activating agent may be one that activates a single blood factor or that activates a pathway such as the intrinsic pathway or extrinsic pathway. Activating agents for activating a specific component of the blood coagulation cascade include, for example, mixtures of or preparations containing phospholipids such as, e.g., negatively charged phospholipids; lipoproteins such as, e.g., thromboplastin, and the like; proteins such as tissue factor, activated serin proteases such as Factors IIa (thrombin), VIIa, IXa, Xa, XIa, XII, XIIa, and protein C, snake venoms such as PROTAC® enzyme, Ecarin, Textarin, Noscarin, Batroxobin, Thrombocytin, Russell's viper venom (RVV), and the like. Activating agents that activate the blood coagulation cascade or a portion thereof include, for example, mixtures of or preparations containing Factor IIa (thrombin), phospholipids such as, e.g., negatively charged phospholipids; calcium ions, tissue factor, unspecific activators such as silica, kaolin, ellagic acid, celite, and so forth. Some specific examples of activation agents include, by way of illustration and not limitation, the following: Kaolin or ellagic acid or silica or celite, negatively charged phospholipids, and calcium ions, which, when used in combination, initiate the reactions involved in the intrinsic pathway, i.e. the aPTT test; thromboplastin (i.e. tissue factor), negatively charged phospholipids and calcium ions, which, when used in combination, initiate the reactions involved in the extrinsic pathway, i.e. the PT test.

The amount of the activating agent is that which is sufficient to activate the component of the blood coagulation cascade or the blood coagulation cascade itself. The amount depends on the nature of the proteolytic coagulation factor to be activated, the nature of the blood coagulation cascade, the nature of the test method to be performed, the scale of the test reaction, and so forth. Thus, the particular amount of activation agent employed in a method in accordance with the present embodiments is determined from a consideration of the above factors and may be determined empirically.

The activation step may require an incubation period of sufficient length to achieve a level of activation such that a determination may be made of the activity of a proteolytic coagulation factor. The duration and other conditions of the incubation period are dependent on the nature of the activating agent, the nature of the component to be activated, the nature of the blood coagulation cascade, the nature of the test to be performed, and so forth. Thus, the duration and other conditions in a particular method in accordance with the present embodiments is determined from a consideration of the above factors and may be determined empirically. The activation may require additional materials that work in concert with the activating agent. Such additional materials include, for example, proteins, buffers, salt, detergents, ions, reducing agents, chelating agents, and so forth.

In the present methods agents are employed to determine the activity of a proteolytic coagulation factor or to determine the activity, presence and/or amount of a component of the blood coagulation cascade. The agents comprise three entities: a cleavable moiety wherein the cleavable moiety has a cleavage site that is cleavable by an activated proteolytic coagulation factor, a chemiluminescent agent and a sensitizer agent. The chemiluminescent agent and the sensitizer agent are related in that, when in close proximity, energizing the sensitizer agent results in energizing the chemiluminescent agent.

The cleavable moiety is any moiety, the cleavage of which can be related to the activity of a proteolytic coagulation factor of the blood coagulation cascade. Thus, the nature of the cleavable moiety is dependent on the nature of the proteolytic coagulation factor of the blood coagulation cascade to be determined. The cleavable moiety may be a synthetic material or a naturally occurring material. The cleavable moiety has a cleavage site that is cleavable by a proteolytic coagulation factor where the cleavage of the cleavage site is directly related to the presence and activity of a specific proteolytic coagulation factor. The cleavable moiety comprises a means for binding the cleavable moiety to the chemiluminescent agent and for binding the cleavable moiety to the sensitizer agent.

In some embodiments the cleavable moiety is a synthetic entity that is added to the reaction mixture. In some embodiments at least the cleavage site of the cleavable moiety is a peptide, i.e., the cleavage site is composed primarily of amino acids. The entire cleavable moiety may be a peptide wherein a portion of the peptide comprises a cleavage site. Thus, the cleavable moiety may be partially or solely peptidic. On the other hand, a cleavage site that is a peptide may be part of a cleavable moiety that comprises a non-peptidic chain wherein the non-peptidic chain comprises non-amino acid members, which may provide linking to another entity such as, for example, to a particle, member of a specific binding pair, and the like. A peptidic cleavage site may be present at any position within a peptidic or non-peptidic chain with the primary consideration being that cleavage of the cleavable site results in the chemiluminescent reagent and the sensitizer reagent not being in close proximity. The length of a cleavage site that is a peptide is at least about 3 monomeric units (usually, amino acid units) and no more than about 150 monomeric units, or at least 5 monomeric units and no more than about 130 monomeric units. The length of a chain of atoms in a non-peptidic chain, including the peptidic cleavage site, may be about 5 to about 5000 atoms. The length of a chain in a peptidic chain, including the peptidic cleavage site, may be about 5 to about 5000 monomeric units.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The cleavable moiety may itself be a component of the blood coagulation cascade such as a coagulation factor or a portion thereof that is present endogenously in a sample or is added as a separate reagent. Examples of such cleavable moieties, by way of illustration and not limitation include moieties present in or consisting of Factor V, which is specifically cleaved by activated protein C, Factor Xa, thrombin or plasmin; fibrinogen, which is specifically cleaved by thrombin; Factor II (prothrombin), which is cleaved by Factor IIa (thrombin), Factor Xa, or certain snake venoms such as Ecarin or Textarin; Factor V, which is cleaved by thrombin or Factor Xa; Factor VII, which is cleaved by thrombin or Factors VIIa, IXa, Xa or XIIa, respectively; Factor VIII, which is cleaved by thrombin; Factor IX, which is cleaved by Factor VIIa or Factor XIIa; Factor X, which is cleaved by Factor VIIa or Factor IXa or snake venoms such as RVV; Factor XI, which is cleaved by Factor XIIa, thrombin or Factor XIa; Factor XII, which is cleaved by Factor XIIa, kallikrein, plasmin or trypsin; Factor XIII, which is cleaved by thrombin; protein S, which is cleaved by thrombin, and so forth.

In general, the length of the cleavable moiety depends on the sequence requirements of the proteolytic coagulation factor to be determined and the nature of the chemiluminescent agent and the sensitizer agent, and the like. The length is such that there is a significant measurable difference in the signal produced by the energization of the chemiluminescent agent by the sensitizer agent when the two agents are in close proximity (i.e., bound together by the cleavable moiety) as compared with the signal obtained when the chemiluminescent reagent and the sensitizer reagent are not in close proximity (i.e., not bound together by the cleavable moiety). These agents are discussed in more detail below.

Energization of the chemiluminescent agent by the sensitizer agent takes place when the two agents are in close proximity, that is, for example, within a distance range of a few micrometers, in particular within a distance range of less than 600 nm, preferably less than 200 nm.

In the reaction mixture, the cleavable moiety is or becomes bound to the chemiluminescent agent or the sensitizer agent or both. There are various approaches in which the agents can be employed, which are summarized here and discussed in detail below. In one approach, the cleavable moiety and the sample to be analyzed are combined wherein the cleavable moiety is either contained in a separate reagent which is added to the reaction mixture or the cleavable moiety is a natural substrate of the proteolytic coagulation factor which is contained in the sample. The chemiluminescent agent is added after activation of the component(s) of the blood coagulation cascade. Then, the sensitizer reagent is added. Alternatively, the chemiluminescent agent and the cleavable moiety (as a single reagent with the cleavable moiety attached to the chemiluminescent agent or as two reagents wherein the cleavable moiety becomes attached to the chemiluminescent agent in situ, i.e. in the reaction mixture) may be combined with the sample to be analyzed and the proteolytic blood coagulation factor may then be activated followed by addition of the sensitizer agent. In another approach, the sensitizer agent and the cleavable moiety (as a single reagent with the cleavable moiety attached to the sensitizer agent or as two reagents wherein the cleavable moiety becomes attached to the sensitizer agent in situ) may be combined with the sample to be analyzed and the proteolytic blood coagulation factor may then be activated followed by addition of the chemiluminescent agent. In another approach, the chemiluminescent agent, the sensitizer agent and the cleavable moiety (as a single reagent with the cleavable moiety attached to both the chemiluminescent agent and the sensitizer agent (preformed) or as three reagents wherein the cleavable moiety becomes attached to the chemiluminescent agent and the sensitizer agent in situ) may be combined with the sample to be analyzed and the proteolytic blood coagulation factor may then be activated.

In some embodiments the cleavable moiety is combined with the sample to be analyzed, the combination is incubated for a time and under conditions such that the cleavable moiety is cleaved if the sample contains a proteolytic coagulation factor(s) under analysis, (i.e., after activation). The cleavable moiety comprises a means for binding the cleavable moiety to the chemiluminescent agent and for binding the cleavable moiety to the sensitizer agent. Thus, after the incubation period, the chemiluminescent agent is added to the combination and binds to the cleavable moiety or, if the cleavable moiety is cleaved, to a portion of the cleavable moiety, which comprises the means for binding the cleavable moiety and the chemiluminescent agent. The approach wherein the cleavable moiety and the chemiluminescent agent are added separately allows for facile screening of various different cleavable moieties for use in the present methods, and may allow better sterical accessibility of the activated protease to the cleavage moiety.

The means for binding the cleavable moiety and the chemiluminescent agent may include members of a specific binding pair. One member of the specific binding pair is linked to the cleavable moiety and the other member of the specific binding pair is linked to the chemiluminescent agent. A member of a specific binding pair ("sbp member") is one of two different molecules, having an area on the surface or in a cavity, which specifically binds to and is thereby defined as complementary with a particular spatial and polar organization of the other molecule. The members of the specific binding pair may be members of an immunological pair such as antigen-antibody (including monoclonal antibodies), although other specific binding pairs such as biotin-(strept)avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

In some embodiments the means for attaching the cleavable moiety or a portion thereof to the chemiluminescent agent may involve an antigenic or epitopic site on the cleavable moiety and an sbp member on the chemiluminescent agent wherein the sbp member is directed against the antigenic or epitopic site. An sbp member for the antigenic or epitopic site may be present on the chemiluminescent agent by covalent attachment such as by covalent attachment of the sbp member to the chemiluminescent agent. On the other hand, the attachment of the sbp member for the cleavable moiety to the sensitizer agent may be accomplished by the use of a different sbp member pair such as, for example, an antibody directed to the epitopic site of the cleavable moiety attached to biotin where the sensitizer reagent comprises a binding partner for the biotin such as anti-biotin or streptavidin.

In some embodiments the sample is combined with a cleavable moiety, which is already attached to the chemiluminescent agent. In this approach the cleavable moiety may be attached to the chemiluminescent agent by covalent or non-covalent binding. Exemplary of non-covalent binding is the use of an sbp member pair as discussed above.

In some embodiments the cleavable moiety and the chemiluminescent agent may be covalently attached. The attachment may be by a direct bond or through a linking group wherein the cleavable moiety and the chemiluminescent reagent are coupled together by means of one or more covalent bonds. The covalent attachment process can be comprised of any number of steps. The linking group attaching the cleavable moiety and the chemiluminescent agent may comprise one or more functionalities for linking. The linking functionalities can comprise atoms other than hydrogen selected from the group normally consisting of carbon, oxygen, sulfur, nitrogen, and phosphorous. The linking groups may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the cleavable moiety and the chemiluminescent reagent include alkylamine, amidine, thioamide, ether, urea, thiourea, guanidine, azo, thioether and carboxylate, sulfonate, and phosphate esters, amides and thioesters. Various linking groups are well known in the art; see, for example, Cautrecasas, *J. Biol. Chem*. (1970) 245: 3059. Specific linking groups useful in linking components include dicarboxylic acids and anhydrides, polyamines, polyaldehydes, and heterobifunctional agents such as 2-iminothiolane hydrochloride, sulfosuccinimidyl-4-(N-maleimidomethyl)cyclohexane-1-carboxylate, m-maleimidosuccinimide ester, N-succinimidyl-(4-iodoacetyl)aminobenzoate, and similar species known to those skilled in the art.

The length of the linking group linking the cleavable moiety and the chemiluminescent agent is dependent on the considerations discussed above with regard to the length of the cleavable moiety. The linking group may be viewed as part of the cleavable moiety with regard to the overall considerations of length or distance between the chemiluminescent agent and the sensitizer agent.

Following activation of the proteolytic coagulation factor or following activation of the blood coagulation cascade, if the chemiluminescent agent is not already included in the combination either attached to the cleavable moiety or as a separate reagent, which comprises means for attaching to the cleavable moiety, the chemiluminescent agent is added to the combination. Thus, as discussed above, the chemiluminescent agent may be added prior to or subsequent to the activation of the proteolytic coagulation factor or the blood coagulation cascade.

As mentioned above, agents employed in the methods of the present invention also comprise a sensitizer agent that is capable of becoming attached to the cleavable moiety or a portion thereof. Thus, the cleavable moiety includes means for attaching the sensitizer agent. Such means include sbp member interaction as discussed above with regard to the chemiluminescent agent attachment to the cleavable moiety. In general, the means for attaching the chemiluminescent agent and the means for attaching the sensitizer agent to the cleavable moiety are on opposite sides of the cleavage site of the cleavable moiety. By opposite sides is meant that cleavage of the cleavage site by the proteolytic coagulation factor ultimately results in a separate portion of the cleavable moiety that comprises the chemiluminescent agent and a separate portion of the cleavable moiety that comprises the sensitizer agent, which thereby removes the chemiluminescent agent and the sensitizer agent from being in close proximity or does not permit the chemiluminescent agent and the sensitizer being in close proximity.

In some embodiments the means for attaching the cleavable moiety or a portion thereof to the sensitizer agent may involve an antigenic or epitopic site on the cleavable moiety and an sbp member on the sensitizer reagent wherein the sbp member is directed against the antigenic or epitopic site. An sbp member for the antigenic or epitopic site may be present on the sensitizer agent by covalent attachment such as by covalent attachment of the sbp member to the sensitizer agent.

On the other hand, the attachment of the sbp member for the cleavable moiety to the sensitizer agent may be accomplished by the use of a different sbp member pair such as, for example, an antibody directed to the epitopic site of the cleavable moiety attached to biotin where the sensitizer agent comprises a binding partner for the biotin such as anti-biotin or streptavidin.

The sensitizer agent may be any moiety that upon activation produces a product that activates the chemiluminescent composition, which in turn generates a detectable signal. In many embodiments the sensitizer is capable of generating singlet oxygen upon activation. In many embodiments the sensitizer is a photosensitizer for generation of singlet oxygen usually by excitation with light. The photosensitizer includes those entities that can be photoactivated (e.g., dyes and aromatic compounds) or chemi-activated (e.g., enzymes and metal salts). The photosensitizer should absorb light in the wavelength range of about 200 to about 1100 nm, or about 300 to about 1000 nm, or about 450 to about 950 nm, with an extinction coefficient at its absorbance maximum greater than about 500 $M^{-1}$ $cm^{-1}$, or at least about 5000 $M^{-1}$ $cm^{-1}$, or at least about 50,000 $M^{-1}$ $cm^{-1}$ at the excitation wavelength. Photosensitizers that are to be excited by light will be relatively photostable and will not react efficiently with singlet oxygen.

Several structural features are present in most useful photosensitizers. Most photosensitizers that are excited by light have at least one, and frequently three or more, conjugated double or triple bonds held in a rigid, frequently aromatic structure. They may contain at least one group that accelerates intersystem crossing such as a carbonyl or imine group or a heavy atom selected from rows 3-6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents for rendering such compounds more lipophilic or more hydrophilic and/or as attaching groups for attachment, for example, to an sbp member. Examples of other photosensitizers that may be utilized are those set forth in U.S. Pat. Nos. 5,340,716 and 6,153,442, the disclosures of which are incorporated herein by reference.

The chemiluminescent agent comprises a compound that undergoes a chemical reaction upon direct or sensitized excitation by light or upon reaction with singlet oxygen or upon chemical activation to form a metastable reaction product that is capable of decomposition with the simultaneous or subsequent emission of light, usually within the wavelength range of about 250 to about 1200 nm. In some embodiments the chemiluminescent composition comprises a substance that reacts with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes, 2,3-dihydro-1,4-phthalazinediones, 2,4,5-triphenyl-imidazoles, and lucigenin, and the like. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, and the like.

The chemiluminescent compounds preferably emit at a wavelength above 300 nm, preferably above 500 nm, and more preferably above 550 nm. Compounds that absorb and emit light at wavelengths beyond the region where the sample components contribute significantly to light absorption are of particular use in embodiments of the present methods. The electron rich olefins generally have an electron-donating group in conjugation with the olefin. The more preferred olefins are those that yield a dioxetane that decays rapidly at room temperature (less than 60 minutes, preferably less than 5 minutes, desirably less than 30 sec). The dioxetanes may be luminescent alone or in conjunction with a fluorescent energy acceptor.

Other chemiluminescent compounds include fluorophores such as, for example, rhodamines, ethidium bromide, 5-dimethylamino-1-naphthalenesulfonyl, europium (Eu) chelates with the agent 3-(2-thienoyl)-1,1,1-trifluoroacetone (TTA) $(Eu(TTA)_3)$ or ruthenium (Ru) chelates with the agent 2,2'-dipyridyl (byp) $(Ru(bpy)_3)$. Examples of other chemiluminescent compounds that may be utilized are those set forth in U.S. Pat. Nos. 5,340,716 and 6,153,442, the disclosures of which are incorporated herein by reference.

In many embodiments the chemiluminescent agent and the sensitizer agent are each associated with a support. As used herein, the phrase "associated with" includes covalent binding of one moiety to another moiety either by a direct bond or through a linking group, non-covalent binding of one moiety to another moiety either directly or by means of specific binding pair members bound to the moieties, incorporation of one moiety into another moiety such as by dissolving one moiety in another moiety or by synthesis, coating one moiety on another moiety, and so forth.

The support may be comprised of an organic or inorganic, solid or fluid, water insoluble material, which may be transparent or partially transparent. The support can have any of a number of shapes, such as particulate including beads and particles, film, membrane, tube, well, strip, rod, planar surfaces such as, e.g., plate, and the like. In many embodiments, the support is suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly(vinyl chloride), polyacrylamide, polyacrylate, polyethylene, polypropylene, poly(4-methylbutene), polystyrene, polymethacrylate, polyethylene terephthalate), nylon, polyvinyl butyrate), etc.; either used by themselves or in conjunction with other materials.

In some embodiments particles are employed as the supports. The particles may have an average diameter of at least about 0.02 microns and not more than about 100 microns. In some embodiments, the particles have an average diameter from about 0.05 microns to about 20 microns, or from about 0.2 microns to about 10 microns. The particle may be organic or inorganic, swellable or non-swellable, porous or non-porous, solid or containing an internal void, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are latex particles.

The polymer particles can be formed of addition or condensation polymers. The particles will be readily dispersible in an aqueous medium and can be adsorptive or functionalizable so as to permit conjugation to an sbp member or a chemiluminescent compound or a sensitizer compound, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

A chemiluminescent compound and/or a sensitizer compound may be associated with a solid support in any manner known in the art. In some embodiments, the compounds are dissolved in the solid support or in a layer on the solid support. In some embodiments, the compound may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives, or aldehydes or dialdehydes, and so forth. Linking groups may also be used to covalently couple the solid support and the compound. Other methods of binding the compounds are also possible. For instance, a solid support may have a coating of a binder for a small molecule such as, for example, (strept)avidin, an antibody, etc., and a small molecule such as, e.g., biotin, hapten, etc., can be bound to the compound or vice versa. The binding of compounds to the surface of a support may be direct or indirect, covalent or non-covalent and can be accomplished by well-known techniques, commonly available in the literature. See, for example, Cautrecasas, *J. Biol. Chem.*, 245: 3059 (1970).

The concentrations of the various reagents of the reagent system will generally be determined by the concentration range of interest of the component(s) of the blood coagulation cascade, and the like. However, the final concentration of each of the reagents is normally determined empirically to optimize the sensitivity of the assay over the range of interest. That is, a variation in concentration of analyte that is of significance should provide an accurately measurable signal difference. Considerations such as the nature of the agents to be employed and the nature of the component(s) of the blood coagulation cascade normally determine the concentrations of the various reagents.

The function of the agents to be employed is to assist in analyzing for the activity of a proteolytic coagulation factor, which may be related to determining the presence and/or amount and/or activity of one or more components of the blood coagulation cascade. As mentioned above, the effect of the direct or indirect activation of the proteolytic coagulation factor(s) on the agents is evaluated to determine the activity of a proteolytic coagulation factor, which can be related to the presence and/or amount and/or activity of another specific proteolytic coagulation factor or a cofactor. If the one or more components of the blood coagulation cascade that influence(s) the activity of the specific proteolytic coagulation factor is/are not present or not activated, cleavage of the cleavable moiety is either inhibited or activated depending on the nature of the cofactor's influence on the activity of the proteolytic coagulation factor. The reaction mixture containing the combination comprises the chemiluminescent agent and the sensitizer agent attached on different sides of the cleavage site of the cleavable moiety. The signal obtained with the unknown sample is compared to that obtained with a sample known to be lacking the component(s) of the blood coagulation cascade (control) and the difference in the signal amount is related to the presence and/or amount and/or activity of the component(s) in the unknown sample. For the most part the amount of signal from the chemiluminescent compound is inversely proportional to the cleaving activity of the activated proteolytic coagulation factor.

Following the addition of all of the reagents of the reagent system to the reaction mixture and after the appropriate incubation periods as necessary for the cleavage of the cleavage site and other processes, the reaction mixture is treated to energize the sensitizer agent. Energizing of the sensitizer agent depends on the nature of the sensitizer. Energization of the sensitizer agent may be by application of light, heat, chemical agents, and so forth. For a sensitizer agent that is activated by light, the reaction mixture is irradiated with light.

Determining a proteolytic coagulation factor(s) or component(s) of the blood coagulation cascade refers to the quantitative, semiquantitative and qualitative detection of the component(s) or the activity of the component(s). Methods of determining the component(s) may be quantitative, semiquantitative and qualitative. The terms "detecting" and "measuring," as well as other common synonyms for measuring, are contemplated within the scope of the present invention.

The determination of a proteolytic coagulation factor of the blood coagulation cascade involves detection of a signal from the reaction mixture comprising the combination of the aforementioned reagents and sample. The presence and/or amount of the signal are related to the presence and/or amount and/or activity of the component(s) in the sample. The particular mode of detection depends on the nature of the sensitizer and the chemiluminescent agents. As mentioned above, in many embodiments the amount of signal from the chemiluminescent compound is inversely proportional to the cleaving activity of the activated proteolytic coagulation factor.

The examination for presence and/or amount of the signal includes the detection of the signal, which is generally a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount and activity of the component(s) present in a sample. Temperatures during measurements generally range from about 10° C. to about 70° C., or from about 20° C. to about 45° C., or about 20° C. to about 25° C. In one approach standard curves are formed using known concentration(s) of the component(s) to be analyzed. As discussed above, calibrators and other controls may also be used.

When a photosensitizer agent is used, the photosensitizer serves to activate the chemiluminescent agent when the reaction mixture containing the above reactants is irradiated. The reaction mixture is irradiated with light having a wavelength of sufficient energy to convert the photosensitizer to an excited state and render it capable of activating molecular oxygen to singlet oxygen. The photosensitizer agent concentration may be low, about $10^{-6}$ to about $10^{-12}$ M or lower. Generally, for the above embodiments involving a photosensitizer agent, the reaction mixture is irradiated with light having a wavelength of about 300 to about 1200 nm, or about 450 to about 950, or about 550 to about 800 nm. The resulting signal is measured at a wavelength of about 550 to about 800 nm, or about 600 to about 700 nm, or in some embodiments at about 612 nm. The amount of this signal is related to the presence and/or amount and/or activity of the component(s) of the blood coagulation cascade in the sample.

The period of irradiation will depend on the lifetime of the activated chemiluminescent agent, the light intensity and the desired emission intensity. For short-lived activated chemiluminescent agent, the period may be less than a second, usually about a millisecond but may be as short as a microsecond where an intense flashlamp or laser is used. For longer-lived activated chemiluminescent agents, the irradiation period can be longer and a less intense steady light source can be used. In general, the integrated light intensity over the period of irradiation should be sufficient to excite at least 0.1% of the photosensitizer molecules, preferably at least 30%, and, most preferably, every photosensitizer molecule will be excited at least once.

The luminescence or light produced in any of the above approaches can be measured visually, photographically, actinometrically, spectrophotometrically or by any other convenient means to determine the amount thereof, which is related to the amount of analyte in the medium.

A helium-neon laser is an inexpensive light source for excitation at 632.6 nm. Photosensitizers that absorb light at this wavelength are compatible with the emission line of a helium-neon laser and are, therefore, particularly useful in the present methods in which photosensitizers are employed. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

Specific Embodiments of Assays

The following specific embodiments of methods for analyzing for one or more components of the blood coagulation cascade are provided for purposes of illustration and not limitation.

Figure 1:
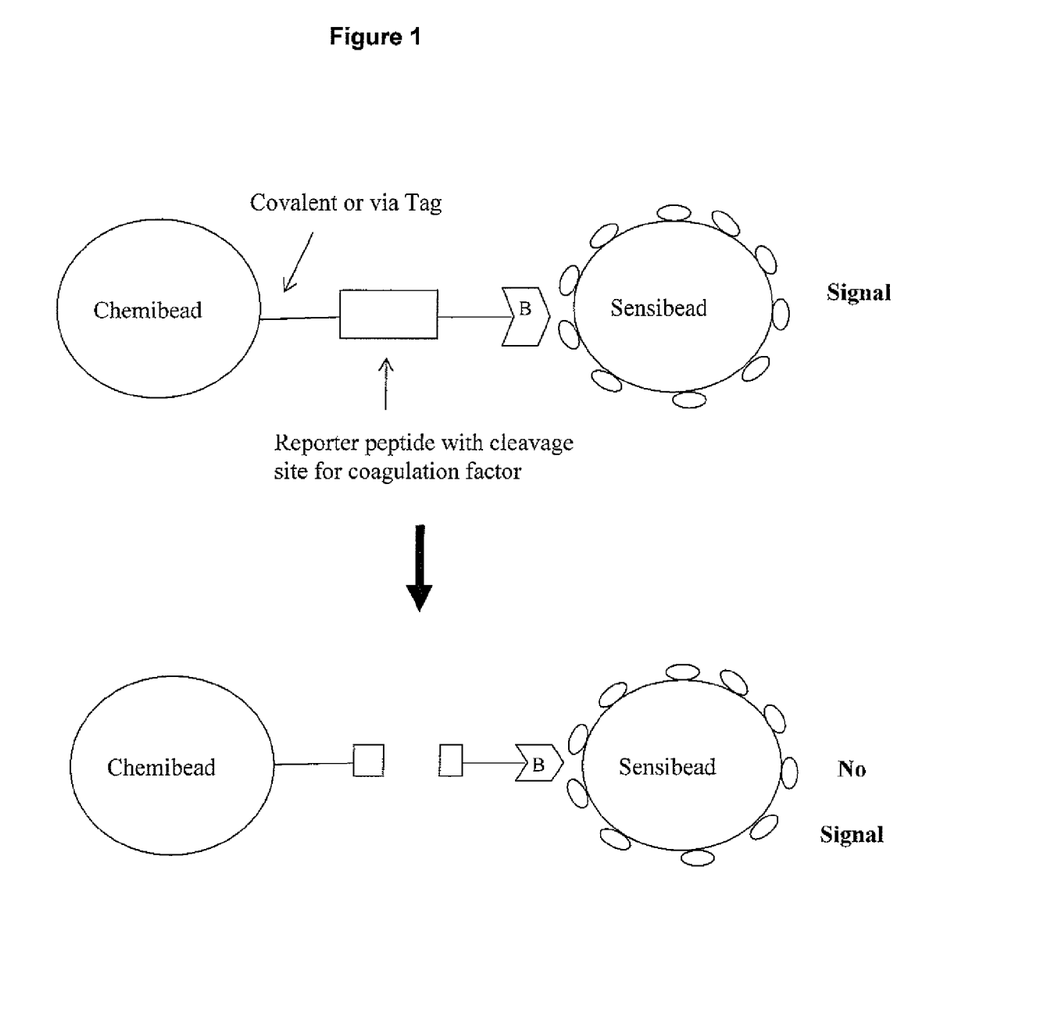
FIG. 1 illustrates an embodiment of the present methods.

In one embodiment of the present methods (referring to FIG. 1), the cleavable moiety is a peptide that contains an epitope on one end and a biotin (B) molecule on the other end. The peptide contains a cleavage site for one of the serin proteases among the coagulation factors. The peptide is incubated with a patient sample, which is a whole blood sample or a plasma sample. (The peptide may also be directly conjugated to the chemiluminescent agent, in which case no epitopic binding pair is required.) Coagulation is then triggered by activators of the extrinsic or intrinsic pathways, or of single factors (by, e.g., Batroxobin). A coagulation factor that is either directly or indirectly activated can then cleave the peptide. After the cleavage, a chemiluminescent agent is added if the peptide is not directly conjugated to the chemiluminescent agent. The chemiluminescent agent is a particle in which a chemiluminescent compound is dissolved (Chemibead); the surface of which is coated with an antibody against an epitope of the peptide which is located on one side of the cleavage site. The sensitizer agent is added to the medium. The sensitizer agent is a particle in which is dissolved a photosensitizer (Sensibead) and to the surface of which is attached a binding partner, such as streptavidin, for the biotin (B) label of the peptide which is located on the opposite side of the cleavage site. The medium is irradiated at 680 nm to energize the photosensitizer. The resulting signal is inversely proportional to the activity of the respective coagulation factor because a strong signal (chemiluminescent agent and photosensitizer agent are in close proximity) indicates that the peptide is not cleaved, hence indicating the absence of an activated factor, whereas a weak signal (chemiluminescent agent and photosensitizer agent are not in close proximity) indicates that the peptide is cleaved, hence indicating the presence or activity of an activated proteolytic coagulation factor. The signal is determined either by the concentration or biochemical activity of the factor itself (if the factor is activated directly) or of the concentrations or biochemical activities of one or more components that influence the activity of the specific proteolytic coagulation factor, e.g. upstream coagulation factors of the blood coagulation cascade (if a pathway or a coagulation factor that acts upstream of the specific proteolytic coagulation factor is activated). The biochemical activities of the coagulation factors of the blood coagulation cascade can be influenced by genetic alterations, acquired synthesis inhibition, therapeutic agents, inhibitory antibodies, defects in required cofactors and so forth, which allows the methods described to be used for both diagnosis and therapy monitoring. In a preferred embodiment of the present methods, the activity of the activated proteolytic coagulation factor is indicative of the presence and/or amount of one or more therapeutic anticoagulants in a patient's sample. The present methods allow for example the determination of direct thrombin inhibitors, such as, for example, hirudin, argatroban or melagatran by combining a patient's sample with an activation agent which activates prothrombin, as for example Ecarin, and with a cleavable moiety, the cleavage of which can be related to the activity of a proteolytically active product of activated prothrombin, such meizothrombin or thrombin. If a direct thrombin inhibitor is present in the sample the activity of a proteolytically active product of activated prothrombin is inhibited and cleavage of the cleavable moiety is reduced.

In another embodiment of the present methods, the activity of both serin protease and non-serin protease coagulation factors can be determined. The peptide (e.g., with a Factor Xa or thrombin-specific cleavage site) is responsive to a serin protease that is downstream (in the blood coagulation cascade) of the coagulation factor that is to be quantified in the respective pathway. The peptide is first incubated with a plasma or whole blood sample that is deficient for the coagulation factor that is to be quantified, plus the patient sample containing an unknown amount of the coagulation factor that is to be quantified. Coagulation is then triggered by activators of the extrinsic or intrinsic pathways, or of single factors (by, e.g. Russel's Viper Venom, RVV). The respective coagulation pathway can only be activated if the coagulation factor that is to be quantified is present in the patient sample, and the amount of activation is directly proportional to the biochemical activity of the respective coagulation factor in the patient sample. After cleavage of the peptide, Chemibeads (as described above) coated with an antibody against the epitope of the peptide are added, if the reporter peptides are not directly conjugated to the Chemibeads. Sensibeads (as described above) are subsequently added, if not added directly to the chemibeads, and the medium is irradiated with light of wavelength 680 nm. The resulting signal is measured and related to the coagulation factor that is to be quantified.

Initial diagnostic testing of patients with suspected bleeding disorders is usually performed with the so-called global coagulation tests, the aPTT and the PT. In addition, these tests are also used for anticoagulant therapy monitoring. While the aPTT is mainly used for detection of deficiencies in factors of the intrinsic pathway and for heparin therapy monitoring, the PT is used for detection of deficiencies in factors of the extrinsic pathway and for vitamin K antagonist therapy monitoring. Both aPTT and PT can also be used for detection of single factor deficiencies by mixing a plasma that is deficient for the coagulation factor that is to be quantified, plus a patient sample containing an unknown amount of the coagulation factor that is to be quantified. Accordingly, embodiments of the present methods may be employed to determine the signal decrease as a consequence of the respective coagulation cascade, which can be related to the time to clot formation that is used by classical aPTT and PT methods.

In the known aPTT reaction, coagulation is initiated in a patient plasma sample by activation of the intrinsic pathway, by addition of a mixture of a contact activator such as ellagic acid or kaolin, and phospholipids and calcium ions. Subsequently, the time until the thrombin that is generated has converted enough fibrinogen to a visible fibrin clot is determined. This known approach is a relatively insensitive detection method that also requires high sample volumes. The present methods avoid these deficiencies of the known approach. In some embodiments of the present methods, the reporter molecule fibrinogen of the known aPTT approach is replaced by thrombin-sensitive peptide fragments derived from a natural thrombin substrate such as Factor XIII, and peptide cleavage is detected by employing a detection system comprising a chemiluminescent agent and a sensitizer agent. In other embodiments of the present methods, a naturally occurring substrate of a specific proteolytic coagulation factor, for instance a thrombin substrate such as Factor XIII which is contained in the patient sample, is used as the cleavable moiety and cleavage of the naturally occurring substrate is detected by employing a detection system comprising a chemiluminescent agent and a sensitizer agent wherein the chemiluminescent agent and the sensitizer agent are able to bind on different sides of the cleavage site of the naturally occurring substrate such as Factor XIII.

In some embodiments the activation agent is used for activating directly a specific proteolytic coagulation factor, the cleavable moiety has a cleavage site that is cleavable by the specific proteolytic coagulation factor and the activity of the specific proteolytic coagulation factor is determined. In some embodiments the activation agent is used for activating the blood coagulation cascade or a part thereof, the cleavable moiety has a cleavage site that is cleavable by a downstream proteolytic coagulation factor of the blood coagulation cascade and the activity of one or more blood coagulation factors that are upstream from the downstream proteolytic coagulation factor is determined. In some embodiments the cleavable moiety has a cleavage site that is cleavable by a downstream proteolytic coagulation factor of the blood coagulation cascade, the sample is suspected of containing a specific coagulation factor that is upstream of the downstream proteolytic coagulation factor, the combination further comprises a known sample that is deficient for the specific coagulation factor, and the activity of the specific coagulation factor is determined by determination of the activity of the downstream proteolytic coagulation factor.

The reagents for conducting a particular method in accordance with the present embodiments may be present in a kit useful for conveniently performing an assay for analyzing the activity of a proteolytic coagulation factor of the blood coagulation cascade. In one embodiment a kit comprises in packaged combination a) an activation agent for activating directly or indirectly a proteolytic coagulation factor of the blood coagulation cascade, b) a chemiluminescent agent, and c) a sensitizer agent. In another embodiment the kit further comprises a cleavable moiety. The agents may be provided as separate entities or conjugate reagents such as, for example, a reagent wherein the chemiluminescent agent is attached to the cleavable moiety. The reagents may each be in separate containers or various reagents can be combined in one or more containers depending on the cross-reactivity and stability of the reagents. The kit can further include other separately packaged reagents for conducting a particular method.

The relative amounts of the various reagents in the kits can be varied widely to provide for concentrations of the reagents that substantially optimize the reactions that need to occur during the present methods and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

As mentioned above, another embodiment of the present invention is a method for assessing an activation property or inhibitory property of a substance on one or more proteolytic coagulation factors of a blood coagulation cascade. A combination is provided in a reaction mixture. The combination comprises a sample containing one or more proteolytic coagulation factors of the blood coagulation cascade, and the substance to be tested. The effect of the combination on a reagent system comprising a cleavable moiety is evaluated. The cleavable moiety has a cleavage site that is cleavable by a proteolytic coagulation factor of the blood coagulation cascade and the cleavable moiety is or becomes bound to a chemiluminescent agent or a sensitizer agent or both. The chemiluminescent agent and the sensitizer agent are related in that, when in close proximity, energization of the sensitizer agent results in energization of the chemiluminescent agent. The effect is related to the activation or inhibitory property of the substance on the one or more proteolytic coagulation factors of the blood coagulation cascade wherein the effect is the extent of cleavage of the cleavable moiety. The above method may be carried out in a manner similar to that described above for the analysis of the activity of a proteolytic coagulation factor including all of the variations discussed above.

The substance to be tested for activating or inhibiting a proteolytic coagulation factor may be a synthetic substance or a naturally occurring substance or a synthetically modified naturally-occurring substance. The substance may be a small molecular thrombin inhibitor such as, e.g. Dabigatran or Argatroban, a heparin or heparin derivative such as fondaparinux, a Factor Xa inhibitor such as, e.g., Danaparoid, a hirudin or derivative thereof, a snake venom, a physiologic inhibitor such as, e.g., antithrombin III or C1 esterase inhibitor, a pharmaceutically active compound and derivatives thereof, tPA or streptase, a plasma factor concentrate such as, e.g., prothrombin complexes or Factor VIII concentrate, an enzyme, a protein, an inhibitory antibody, an ion and so forth.

The following examples further describe the specific embodiments of the present methods by way of illustration and not limitation and are intended to describe and not to limit the scope of the present methods. Parts and percentages disclosed herein are by volume unless otherwise indicated.

EXAMPLES

All chemicals were purchased from the Sigma-Aldrich Company (St. Louis Mo.) unless otherwise noted.

The following peptide was synthesized by means of standard Fmoc chemistry. The cleavable moiety comprised a peptide, which consisted of the FLAG sequence DYKDDDDK at the N-terminus and the thrombin-sensitive sequence derived from human Factor XIII, KLVPRGF, and a C-terminal Glycin residue linked to biotin by means of a spacer group as indicated below. The entire sequence was: DYKD-DDDKLVPRGFG-NHCH$_2$—CH$_2$—NH-Biotin.

The chemiluminescent agent was a particle reagent referred to herein as a Chemibead, which was prepared in a manner similar to the method described in U.S. Pat. No. 6,153,442 and U.S. Patent Application Publication No. 20050118727A, the relevant disclosures of which are incorporated herein by reference. The Chemibead comprised an aminodextran inner layer and a dexal outer layer having free aldehyde functionalities. Dexal is dextran aldehyde; see, for example, U.S. Pat. Nos. 5,929,049 and 7,172,906. The reaction is carried out at a temperature of about 0 to about 40° C., for a period of about 16 to about 64 hours at a pH of about 5.5 to about 7.0, or about 6, in a buffered aqueous medium employing a suitable buffer such as, for example, MES or the like. The reaction was quenched by addition of a suitable quenching agent such as, for example, carboxymethoxy-oxime (CMO), or the like and subsequent washing of the particles. The chemiluminescent compound was 2-(4-(N,N, di-tetradecyl)-anilino-3-phenyl thioxene.

Chemibeads conjugated to the anti-FLAG monoclonal antibody M2 (Sigma, St. Louis) (referred to herein as Chemibead reagent) were manufactured according to the following procedure: The antibody was dialyzed into a buffer (300 mM NaCl, 10 mM phosphate, pH 7.0) using G25 column. Subsequently, TWEEN 20® surfactant was added to a concentration of 0.05%, and antibody was concentrated in a stirred cell concentrator to 20 mg/mL. Two mg antibody was then added to 20 mg Chemibeads, and a covalent linkage was established by addition of 25 mg/mL NaCNBH$_3$. After an incubation step and quenching of the reaction, the conjugated Chemibeads were purified using diafiltration and stored in 50 mM HEPES, 300 mM NaCl, 1 mM EDTA, 0.1% TRITON® X405, 1 mg/mL BSA, 0.15% PROCLIN® 300, 0.1 mg/mL neomycin sulfate, pH 8.0.

The sensitizer agent was a particle reagent referred to herein as Sensibead reagent, which was prepared using a method analogous to that described in U.S. Pat. No. 6,153,442 and U.S. Patent Application Publication No. 20050118727A, the relevant disclosures of which are incorporated herein by reference. The photosensitizer was bis-(trihexyl)-silicon-t-butyl-phthalocyanine.

Example 1

The thrombin-sensitive peptide prepared as described above was dissolved in water to 0-1000 ng/mL. The Chemibead reagent was diluted to 100 µg/mL, the Sensibead reagent to 500 µg/mL in a buffer containing 50 mM HEPES, 300 mM NaCl, 1 mM EDTA, 0.1% TRITON® X405, 1 mg/mL BSA, 0.15% PROCLIN® 300, 0.1 mg/mL neomycin sulfate, pH 8.0. Standard Human Plasma (SHP) and factor-deficient plasmas from Siemens Healthcare Diagnostics Products GmbH (Marburg, Germany) were used and prepared according to the manufacturer's instructions. The plasma samples were diluted manually in 0.9% NaCl immediately prior to the experiment. The recombinant tissue factor based PT reagent INNOVIN® (Siemens Healthcare Diagnostics Products GmbH) was reconstituted in water according to the manufacturer's instruction. In some experiments, 3 mg/mL Clot inhibitor peptide (Bachem, Bubendorf, Switzerland) was added to the INNOVIN® Reagent.

For the test, 10 µl plasma sample, 10 µl peptide and 10 µl INNOVIN® were combined and incubated for 7 min at 37° C. 10 µl Chemibead reagent was added, followed by a 3 min incubation period at 37° C. Subsequently, 10 µl Sensibead reagent was added, and the reaction was incubated for another 6 min at 37° C. The reaction container was then filled with distilled water to 250 µl and illuminated at 680 nm. Chemiluminescent signal was measured for 100 ms at 612 nm using a photodetector from a commercial platform (DIMENSION VISTA®, purchased from Siemens Healthcare Diagnostics Inc., Deerfield, Ill.).

Figure 2:
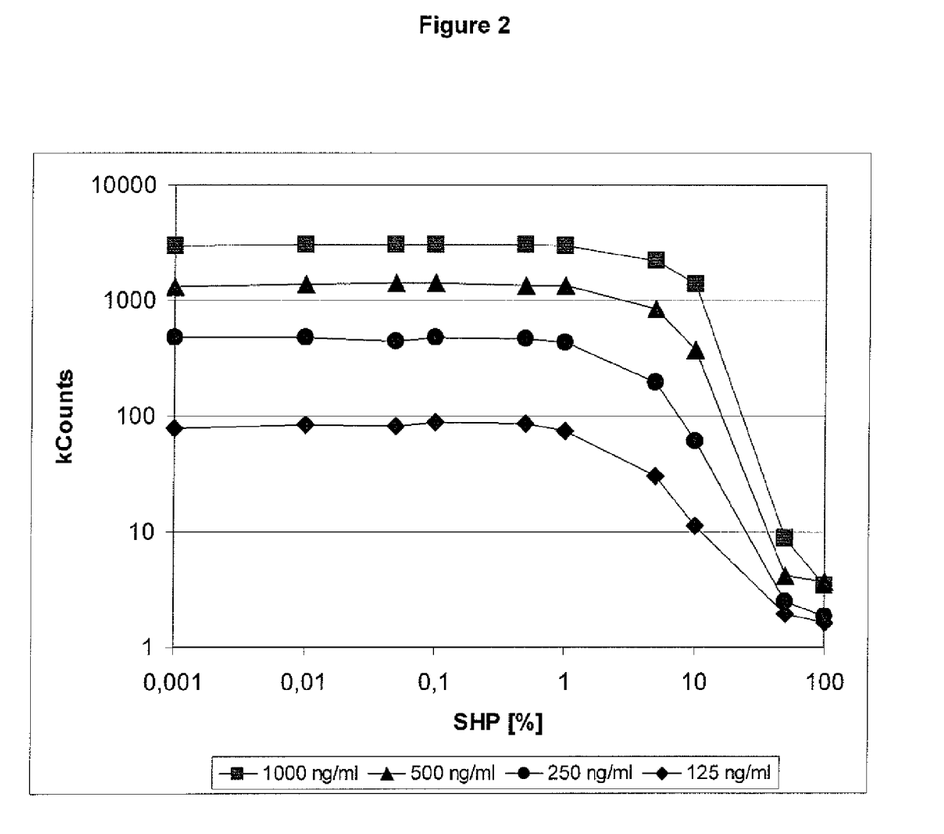
FIG. 2 is a graph depicting results from an experiment summarized in Table 1.

In a first set of experiments, the optimal concentration of the peptide was determined. Several concentrations were tested (see Table 1 where signals are in kcounts). In line with the concept of the present methods, a strong decrease in signal (=activity of the extrinsic pathway) relative to the control performed with 0.9% NaCl was already observed when testing as little as ‰ SHP (=0.1 µl plasma). Although the sensitivity of the test was highest when using 125 ng/mL peptide, 1000 ng/mL peptide gave the strongest overall signal and was taken for subsequent tests. A graphic representation of the data is shown in FIG. 2.

TABLE 1

| SHP % | 1000 ng/ml | 500 ng/ml | 250 ng/ml | 125 ng/ml |
|---|---|---|---|---|
| 0 | 2981 | 1311 | 475 | 78 |
| 0.01 | 3053 | 1387 | 476 | 85 |
| 0.05 | 3026 | 1401 | 447 | 82 |
| 0.1 | 3025 | 1399 | 475 | 88 |
| 0.5 | 3063 | 1357 | 460 | 85 |
| 1 | 2939 | 1348 | 429 | 74 |
| 5 | 2199 | 841 | 197 | 31 |
| 10 | 1372 | 372 | 61 | 11 |
| 50 | 9 | 4 | 2 | 2 |
| 100 | 3 | 4 | 2 | 2 |

To test if the SHP-dependent decrease in signal was caused by the activation of the extrinsic pathway, a control experiment was performed in which single components were left out. These tests demonstrated that the decrease in signal was dependent on both SHP (contains components of the extrinsic pathway) and INNOVIN® (is an activator of the extrinsic pathway), and that the signal was dependent on the peptide (see Table 2, signals are in kcounts). The clot inhibitor peptide was not necessarily required, indicating that coagulation of the diluted plasma samples did not occur or did not influence the signal reaction.

TABLE 2

| Controls | | SHP % | 1000 ng/ml | 500 ng/ml |
|---|---|---|---|---|
| +Innovin | | NaCl | 3007 | 1346 |
| +Clot inhibitor | | 1 | 3015 | 1319 |
| | | 10 | 1532 | 361 |
| | | 100 | 4 | 3 |
| −Innovin | | NaCl | 3996 | 2323 |
| +Clot inhibitor | | 1 | 4006 | 2338 |
| | | 10 | 3921 | 2238 |
| | | 100 | 3432 | 1910 |
| +Innovin | | NaCl | 3374 | 1656 |
| −Clot inhibitor | | 1 | 3337 | 1574 |
| | | 10 | 416 | 50 |
| | | 100 | 8 | 5 |
| No peptide | | NaCl | 4 | — |
| | | 1 | 3 | — |
| | | 10 | 2 | — |
| | | 100 | 2 | — |

The following test determined that the decrease in signal of the test system may be used to detect deficiencies in coagulation factors of the extrinsic pathway. Deficiencies in Factors VII, X or prothrombin, respectively, in plasma samples lead to a reduced cleavage of the thrombin-sensitive peptide when compared to SHP, which contained all factors of the extrinsic pathway. In contrast, deficiency in Factor VIII or IX, both constituents of the intrinsic pathway, had little or no impact on the peptide cleavage.

Figure 3:
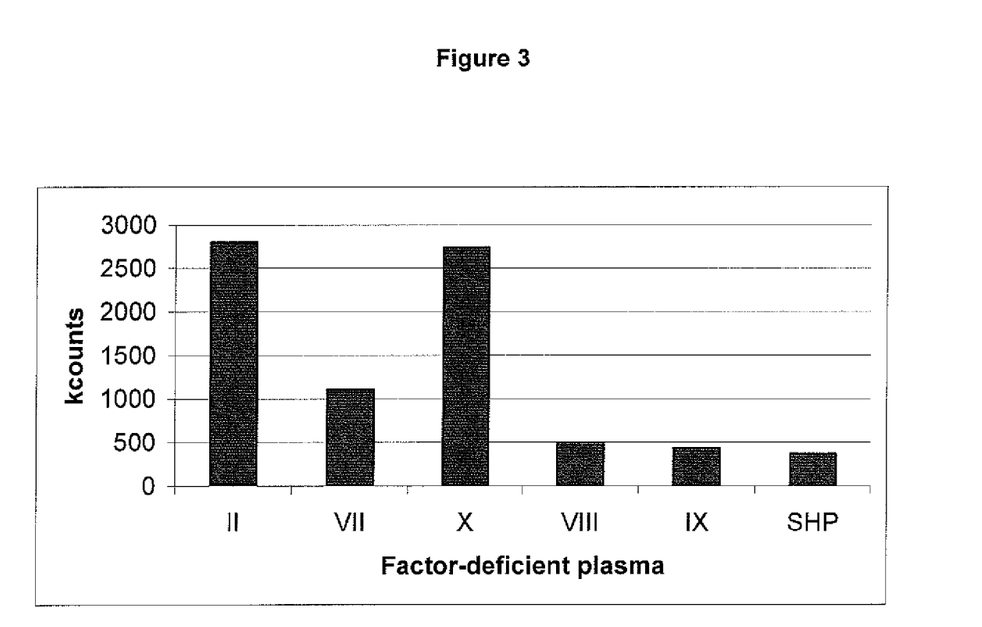
FIG. 3 is a diagram depicting signals generated with factor-deficient plasmas when a PT reagent triggers the extrinsic pathway.

As shown in FIG. 3, the experimental data obtained with 1:5 plasma dilutions confirmed the above. In comparison to the control reaction with SHP, the signal was higher when testing plasma samples deficient in Factors VII, X or prothrombin, respectively. In contrast, plasma samples deficient in Factors VIII or IX, which are not components of the extrinsic pathway, showed a signal level comparable to SHP. These data show that the test system may be used as a global coagulation test (screening) to detect a deficiency in factors of the extrinsic pathway. In contrast to a classical PT reaction, less than a 1/10 sample volume was required, which reduces problems associated with high sample volumes (HIL samples, high sample consumption, which does not permit whole blood assays).

Example 2

The thrombin-sensitive peptide prepared as described above was dissolved in water to 0-1000 ng/mL. The Chemibead reagent was diluted to 100 μg/mL, the Sensibead reagent to 500 μg/mL in a buffer containing 50 mM HEPES, 300 mM NaCl, 1 mM EDTA, 0.1% Triton X® 405, 1 mg/mL BSA, 0.15% Proclin® 300, 0.1 mg/mL neomycin sulfate, pH 8.0. Standard Human Plasma (SHP) and factor-deficient plasmas from Siemens Healthcare Diagnostics Products GmbH were used and prepared according to the manufacturer's instructions. The plasma samples were diluted manually in 0.9% NaCl immediately prior to the experiment. The aPTT reagent Pathromtin SL®, (Siemens Healthcare Diagnostics Products GmbH) containing phospholipids and silicon dioxide activator was prepared according to the manufacturer's instruction, and supplemented with 3 mg/mL Clot inhibitor peptide (Bachem).

For the test, 10 μl plasma sample and 10 μl Pathromtin SL® were combined and incubated for 7 min at 37° C. 10 μl 50 mM CaCl$_2$ and 20 μl anti-FLAG-conjugated Chemibead reagent was added, followed by 3 min incubation at 37° C. Subsequently, 20 μl of the Sensibead reagent was added, and the reaction was incubated for an other 6 min at 37° C. The reaction vessel was then filled with distilled water and illuminated at 680 nm. Chemiluminescent signal was measured for 100 ms.

In a first set of experiments, the optimal concentration of the peptide was determined. Two concentrations were tested (see Table 3, signals in kcounts). In line with the present embodiments, a strong decrease in signal (=activity of the extrinsic pathway) relative to the control performed with 0.9% NaCl was observed. 1000 ng/mL peptide gave the strongest overall signal and was taken for subsequent tests.

TABLE 3

| SHP % | 1000 ng/ml | 100 ng/ml |
| --- | --- | --- |
| 0 | 567 | 39 |
| 100 | 7 | 1 |

The following experiments showed that the decrease in signal of this embodiment of the present test system can be used to detect deficiencies in coagulation factors of the intrinsic pathway. Deficiency in Factors VIII, XI, X, XI or thrombin, respectively, in plasma samples result in a reduced cleavage of the peptide when compared to SHP, which contains all factors of the extrinsic pathway. In contrast, deficiency in Factor VII should have little or no impact on the peptide cleavage.

Figure 4:
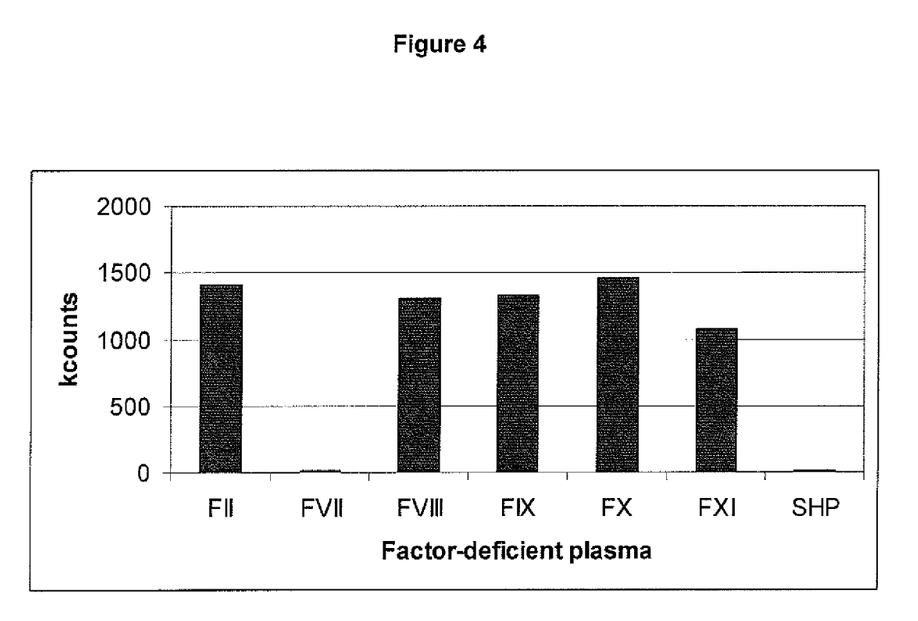
FIG. 4 is a diagram depicting signals generated with factor-deficient plasmas when an aPTT reagent triggers the intrinsic pathway.

As shown in FIG. 4, the experimental data obtained with plasma dilutions demonstrated the above results. In comparison to the control reaction with SHP or factor VII-deficient plasma, the signal was higher when testing plasma samples deficient in Factors VIII, XI, X, XI or thrombin, respectively, meaning that these factors are required for cleavage of the peptide. This assay performed well in detecting the deficiency of factors involved in the intrinsic pathway.

To allow a comparison of the results obtained for conventional PT and aPTT assays to the results of the aforementioned peptide cleavage rates obtained in the assays described above in accordance with the present methods, the present assay and the conventional assay that are performed with the same reagent are calibrated with dilutions of a normal plasma pool such as standard human plasma. For each dilution, the respective chemiluminescent signal and coagulation time are correlated. In this manner, a calibration curve is generated whereby coagulation times are correlated to chemiluminescent signals. An unknown sample that is measured by one of the embodiments of the present methods, therefore, can be correlated to the respective conventional method.

Example 3

The thrombin-sensitive peptide prepared as described above was dissolved in water to 1 μg/mL. The Chemibead reagent as described above was diluted to 100 μg/mL, the Sensibead reagent as described above was diluted to 500 μg/mL in a buffer containing 50 mM HEPES, 300 mM NaCl, 1 mM EDTA, 0.1% Triton X® 405, 1 mg/mL BSA, 0.15% Proclin® 300, 0.1 mg/mL neomycin sulfate, pH 8.0. Standard Human Plasma (SHP) from Siemens Healthcare Diagnostics Products GmbH was used and prepared according to the manufacturer's instructions. The plasma samples were diluted manually in 0.9% NaCl immediately prior to the experiment. The snake venom Ecarin was purchased from Pentapharm (Basel, Switzerland) and prepared according to the manufacturer's instructions. The direct thrombin inhibitors hirudin (purchased from Pharmion as Refludan) and melagatran (purchased from Astra Zeneca) were prepared according to the manufacturer's instructions.

For the test method, 10 μl of diluted plasma samples and 10 μl Ecarin (0.6-2 U/mL) were combined and incubated for 7 min at 37° C. 20 μl anti-FLAG-conjugated Chemibead reagent and 10 μl Sensibead reagent were added, and the reaction mixture was incubated for another 6 min at 37° C. The reaction mixture was then filled up with distilled water and illuminated at 680 nm. Chemiluminescent signal was measured for 100 ms.

Figure 5:
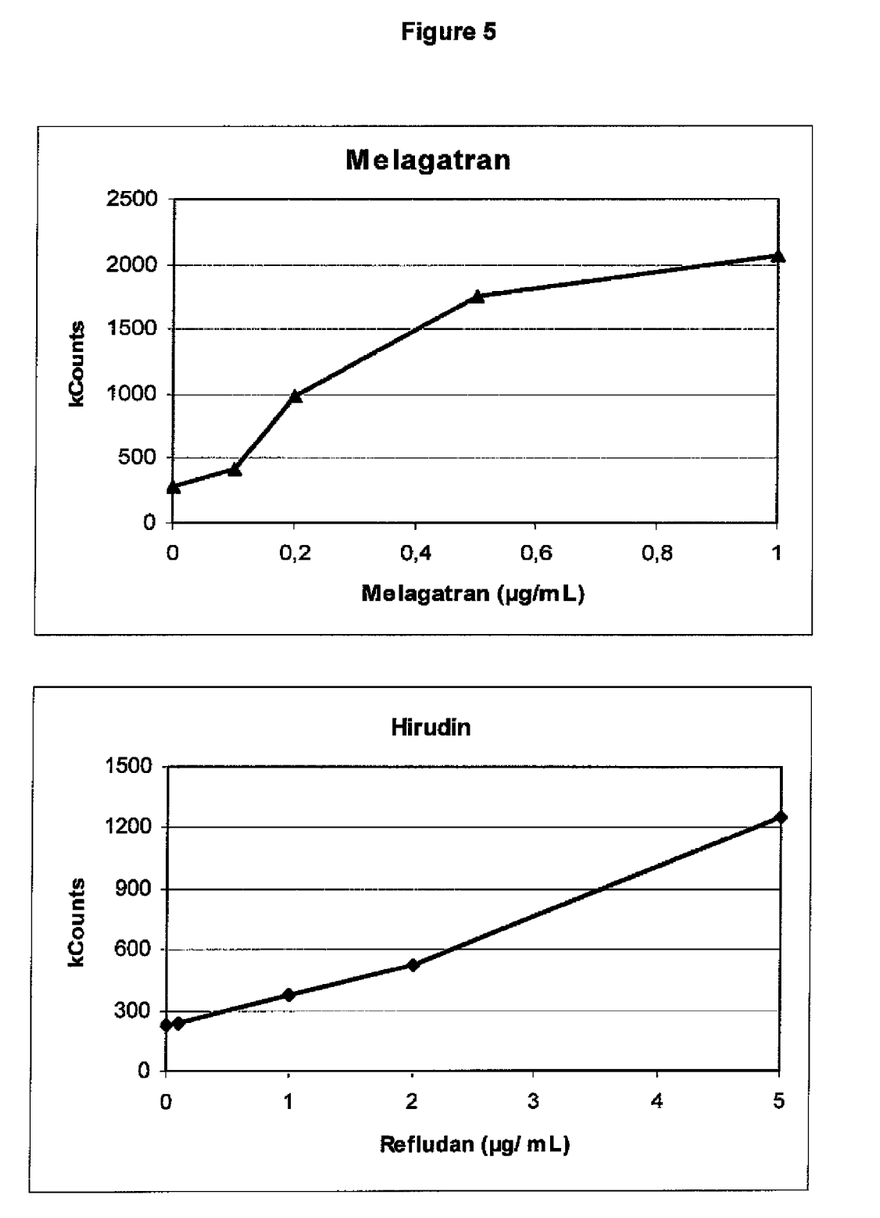
FIG. 5 shows a diagram depicting signals generated with plasma spiked with the direct thrombin inhibitor melagatran (upper diagram) and a diagram depicting signals generated with plasma spiked with the direct thrombin inhibitor hirudin (Refludan) (lower diagram) when Ecarin triggers prothrombin activation.

In a first set of experiments, the effect of the addition of direct thrombin inhibitors to standard human plasma on the chemiluminescent signal was determined in the test setting described above. SHP samples were spiked with different amounts of hirudin or melagatran, and tested as 1:4 dilutions (diluted with 0.9% NaCl) in the test setting described above. As shown in FIG. 5 the presence of therapeutically relevant concentrations of melagatran or hirudin leads to a concentration-dependent reduced cleavage of the peptide resulting in higher chemiluminescent signals when compared to an SHP sample without the respective inhibitor. Hence, this assay can detect the presence of direct thrombin inhibitors.

Figure 6:
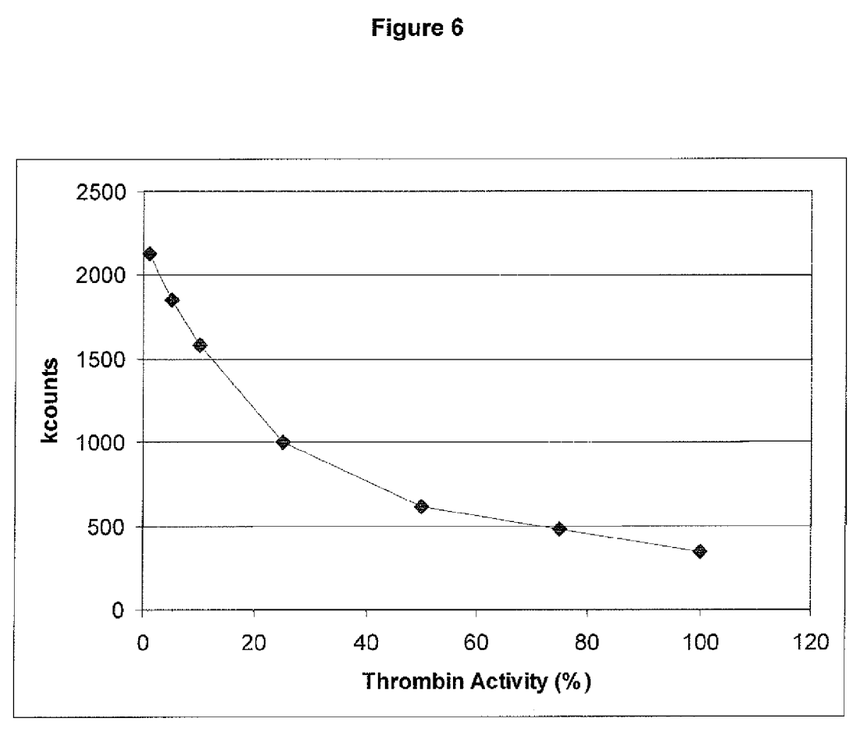
FIG. 6 is a diagram depicting signals generated with dilutions of standard human plasma (reference curve) when Ecarin triggers prothrombin activation.

In order to allow a quantitative determination of the concentration of a direct thrombin inhibitor in a plasma sample, the assay described above was calibrated with dilutions of SHP. Prothrombin activation was performed with Ecarin diluted to 0.6 U/mL. A typical reference curve is shown in FIG. 6. The thrombin activity of undiluted SHP was arbitrarily set to 100%. SHP samples spiked with 0.1 µg/mL or 1 µg/mL hirudin were then tested in the same setup. The chemiluminescent signals of the spiked samples were then compared to the respective value of the reference curve, whereby thrombin activity values were assigned to the spiked samples. The sample spiked with 0.1 µg/mL hirudin, which is a subtherapeutic concentration, was determined with 445 kcounts which corresponds to a residual thrombin activity of 79.5% compared to 100% of the unspiked sample. The sample spiked with 1 µg/mL hirudin, which is a therapeutically relevant concentration, was determined with 914 kcounts which corresponds to a residual thrombin activity of 32.3% compared to 100% of the unspiked sample. Hence, the concentration of the direct thrombin inhibitor hirudin can be quantified by the present method.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for determining the activity of a proteolytic coagulation factor of the blood coagulation cascade in a whole blood or plasma sample, the method comprising:
   (a) providing in combination in a reaction mixture:
      (i) the sample, and
      (ii) an activation agent for activating directly or indirectly the proteolytic coagulation factor of the blood coagulation cascade thereby providing an activated proteolytic coagulation factor,
      (iii) a cleavable moiety which has a cleavage site that is cleavable by the activated proteolytic coagulation factor and wherein the cleavable moiety becomes bound to a chemiluminescent agent and a sensitizer agent,
      (iv) a chemiluminescent agent comprising a member of a specific binding pair capable of interacting with an antigenic or epitopic site on said cleavable moiety, and
      (v) a sensitizer agent comprising a member of a specific binding pair capable of interacting with an antigenic or epitopic site on said cleavable moiety,
      wherein the cleavable moiety is a natural substrate of the activated proteolytic coagulation factor which is contained in the sample and which becomes bound to the chemiluminescent agent and the sensitizer agent in the reaction mixture; and
      wherein the chemiluminescent agent and the sensitizer agent are related in that, when in close proximity, energization of the sensitizer agent results in energization of the chemiluminescent agent;
   (b) measuring a chemiluminescent signal and relating the signal to the activity of the proteolytic coagulation factor of the blood coagulation cascade.

2. The method of claim 1 wherein the sensitizer agent is a photosensitizer that generates singlet oxygen upon irradiation and the singlet oxygen energizes the chemiluminescent agent.

3. The method of claim 1 wherein the chemiluminescent agent comprises a particle having associated therewith a chemiluminescent compound.

4. The method of claim 1 wherein the sensitizer agent comprises a particle having associated therewith a sensitizer compound.

5. The method of claim 1 wherein the chemiluminescent signal is inversely proportional to the activity of the activated proteolytic coagulation factor.

6. The method of claim 1 wherein the proteolytic coagulation factor is selected from the group consisting of Factor II, Factor VII, Factor IX, Factor X, Factor XI, Factor XII and protein C.

7. The method of claim 1 wherein the activation agent for activating directly or indirectly the proteolytic coagulation factor is selected from the group consisting of thromboplastin, Factor IIa, Factor VIIa, Factor IXa, Factor Xa, Factor XIa, Factor XIIa, activated protein C, snake venoms, negatively charged phospholipids, calcium ions, tissue factor, silica, kaolin, ellagic acid and celite.

8. The method according to claim 1 wherein the activity of the activated proteolytic coagulation factor is indicative of the presence or activity of one or more components of the sample to be analyzed that influence the activity of the proteolytic coagulation factor.

9. The method according to claim 1 wherein additionally a plasma or whole blood is added to the reaction mixture which is deficient in a single component which influences the activity of the proteolytic coagulation factor to be determined and wherein the activity of the proteolytic coagulation factor to be determined is indicative of said single component in the sample.

10. The method according to claim 1 wherein the activity of the activated proteolytic coagulation factor is indicative of the functionality of the intrinsic pathway of the blood coagulation cascade.

11. The method according to claim 1 wherein the activity of the activated proteolytic coagulation factor is indicative of the functionality of the extrinsic pathway of the blood coagulation cascade.

12. The method according to claim 1 wherein the activity of the activated proteolytic coagulation factor is indicative of the presence of one or more therapeutic anticoagulants.

* * * * *